United States Patent
Sato

(10) Patent No.: US 7,767,412 B2
(45) Date of Patent: Aug. 3, 2010

(54) DETECTING METHOD FOR THE SEEDS CONTAMINATED WITH PLANT PATHOGENS

(75) Inventor: Masatoshi Sato, Ibaraki-ken (JP)

(73) Assignee: National Center for Seeds and Seedlings, Ibaraki-ken (JP)

( * ) Notice: Subject to any disclaimer, the term of this patent is extended or adjusted under 35 U.S.C. 154(b) by 170 days.

(21) Appl. No.: 11/602,273

(22) Filed: Nov. 21, 2006

(65) Prior Publication Data
US 2007/0190594 A1 Aug. 16, 2007

(30) Foreign Application Priority Data
Feb. 13, 2006 (JP) ............................. 2006-034755

(51) Int. Cl.
*C12Q 1/04* (2006.01)
*C12Q 1/68* (2006.01)
*C12Q 1/24* (2006.01)
*A01C 1/00* (2006.01)

(52) U.S. Cl. ..................... 435/34; 435/419; 435/254.11; 424/93.5

(58) Field of Classification Search ........................ None
See application file for complete search history.

(56) References Cited

U.S. PATENT DOCUMENTS

| 3,833,735 | A  | * | 9/1974 | Iwata et al. ................. 514/739 |
| 2004/0033621 | A1 | * | 2/2004 | Kennedy et al. ............. 436/514 |
| 2006/0179711 | A1 | * | 8/2006 | Bissonnette et al. ......... 47/62 A |
| 2006/0240458 | A1 | * | 10/2006 | Steichen et al. ............... 435/6 |

OTHER PUBLICATIONS

Development of Methods To Control Bacterial Fruit Blotch in Watermelons, Forestry and Fisheries Research Council, Dec. 2002, pp. 13-18 and 24-34, Tokyo, Japan.

* cited by examiner

*Primary Examiner*—Lisa J Hobbs
(74) *Attorney, Agent, or Firm*—Jean C. Edwards, Esq.; Akerman Senterfitt

(57) ABSTRACT

A method of easily detecting a slight percentage of seeds contaminated with a seed-transmissible pathogen as mixed in among a large number of seeds is provided. The method comprises placing a substratum for germination with seeds disposed thereon in a hermetic container, adding an extractant to the hermetic container after germination of the seeds, mixing up the seedlings resulting from germination of the seeds, the germination substratum and the extractant with stirring and/or pressing, and using the mixed liquid derived therefrom as a test material for detecting pathogenic bacteria possibly occurring therein.

11 Claims, No Drawings

DETECTING METHOD FOR THE SEEDS CONTAMINATED WITH PLANT PATHOGENS

CROSS-REFERENCE TO RELATED APPLICATIONS

The present application claims priority from Japanese Patent Application No. JP 2006-034755, filed Feb. 13, 2006, the contents of which are herein incorporated by reference in their entirety.

BACKGROUND OF THE INVENTION

1. Field of the Invention

This invention relates to a method for the detection of plant pathogens in seeds and, more particularly, to a method of detecting seed-transmitted plant pathogens.

2. Description of the Related Art

Plant pathogens spread in the manner of aerial infection, contact transmission or rainwater transmission, and the like, and cause great damage to agricultural productions. Among them, seed-transmissible pathogens, which are serious as primary sources of infection of diseases, do a lot of damage even through a seeds-lot with a low degree of contamination, and the damage is sometimes especially serious in transplant production facilities where a large number of seedlings are raised or in graft cultivation. These seed-transmissible plant pathogens cause various diseases, including bacterial fruit blotch of cucurbit and bacterial brown stripe of rice, and the damage caused thereby is not slight.

The main sources of infection causing such seed-transmitted diseases are seeds contaminated with the corresponding pathogens. A conventional method of detecting contaminated seeds is the grow-out test or sweatbox grow-out test which comprises sowing seeds in compost in a greenhouse or in a plastic box and, after germination, evaluating the seedlings by the occurrence or nonoccurrence of some disease symptom or other. Also known are the methods comprising immersing seeds in a solution and stirring and/or pressing the mixture for washing seeds, using the seed washings solution as such or preparing such a solution by a certain period of incubation at a certain temperature, and using the solution as a sample and subjecting the same to identification of colonies grown on medium, serological detection, genetic diagnosis, or a combination of some of these (cf. e.g. Non-Patent Document: Agriculture, Forestry and Fisheries Research Council Secretariat (December 2002): Development of methods to control bacterial fruit blotch in watermelon, Agriculture, Forestry and Fisheries Research Council, Tokyo).

In carrying out the grow-out test mentioned above, it is necessary to appropriately control the greenhouse conditions to maintain the temperature and humidity in the greenhouse at certain respective levels suited for the growth of seed-transmissible pathogens and the symptom development. The sweatbox grow-out test, which is an improved version of the grow-out test, is carried out in an artificial environment, so that the environment is always under adequate control; since, however, it is necessary to test at least 10000 or more seeds, the facilities required for inspection constitute a heavy burden from the equipment and cost viewpoint.

The percent germination of the seeds to be inspected is not always 100% and, in case of the only or all the contaminated seeds failing to germinate, there arises the problem that the seeds of the relevant lot are erroneously evaluated as healthy and safe. Furthermore, each seed-transmissible pathogen species generally includes several strains, either stronger or weaker in pathogenicity in a crop species; therefore, there is another problem that if there is a contaminated seed but the seedling therefrom is symptomless, the seeds of the relevant lot are evaluated as healthy and safe. Thus, it has been earnestly demanded that a highly precise seed health testing method be developed.

BRIEF SUMMARY OF THE INVENTION

It is an object of the present invention to provide a method of precisely and efficiently detecting a tiny percentage of seeds contaminated with plant pathogens as mixed up with a large number of seeds.

The present inventors found that when the seeds to be tested are allowed to germinate in a hermetic container with the germination substratum or growing medium for germination (hereinafter collectively referred to as "germination substratum") and then the seeds after germination, the germination substratum, and an extractant (extracting solvent) are mixed up with stirring and/or pressing, and the resulting mixture is used as a test material, a pathogen, if present, can be easily detected among a large number of seeds; based on such finding, they have now completed the present invention. Thus, the invention can be defined as follows:

<1> A method of testing seeds as to whether they bear a seed-transmissible pathogen or pathogens which comprises placing the germination substratum sown with seeds to be tested in a hermetic container, allowing the seeds to germinate in the hermetic container, adding an extractant to the container, mixing up the seedlings resulting from germination of the seeds, the germination substratum and the extractant with stirring and/or pressing, and subjecting the mixed liquid derived therefrom, as a test sample, to a pathogen detecting test.

<2> A method as mentioned above, wherein the germination substratum preferably comprises a highly water-absorbing paper and/or a nonwoven fabric and/or cut pieces of a highly water-absorbing paper and/or of a nonwoven fabric.

<3> A method as mentioned above, wherein the germination of the seeds and the growth of the seedlings are preferably realized by causing the germination substratum to absorb water or 0.001-0.03 M phosphate buffer while replacing the air within the hermetic container with fresh air from time to time.

<4> A method as mentioned above, wherein the extractant is preferably water or 0.001-0.03 M phosphate buffer and wherein the pathogen detecting test is preferably based on an identification of colonies grown on medium and/or a serological detection and/or a genetic diagnosis.

The present invention does not require the soil or compost conventionally used in the grow-out test or the like but uses highly water-absorbing papers in ordinary use, for example paper towels; according to the invention, a container with test seeds placed therein is placed in a room maintained at a predetermined temperature and the container inside is maintained at a high humidity level to thereby increase the pathogen population in the container. The invention thus makes it possible to detect a very small percentage of contaminated seeds mixed in among a lot of seeds in a very economical manner.

DETAILED DESCRIPTION OF THE INVENTION

The invention consists in a method of detecting seed-transmissible pathogen-bearing seeds which is characterized in that water is fed to seeds disposed on a substratum for germination in a hermetic container and, after germination, the seedlings from the seeds after germination and an extractant are mixed up with stirring and/or pressing, and the resulting mixed liquid is used as a test sample. Certain specific modes of embodiment of the invention are described below.

The germination of seeds is realized by disposing seeds to be tested on a substratum for germination and allowing the germination substratum to absorb water. The germination substratum may be any of materials capable of retaining moisture, for example cotton cloths, nonwoven fabrics, pulp, sand, polyester products and the like. Among them, pulp, filter paper, paper towels and like highly water-absorbing paper species and/or nonwoven fabrics are more preferred.

The size of the germination substratum can be arbitrarily selected according to the size and number of seeds to be tested. The thickness of the germination substratum should be such that water may be absorbed in an amount required according to the size of seeds to be tested; when a highly water-absorbing paper and/or a nonwoven fabric is used, the required thickness can be obtained by laying a plurality of such substratum layers one on top of another. In cases where the seeds to be tested are large in size, small pieces of a highly water-absorbing paper and/or a nonwoven fabric as cut by means of a shredder or the like are particularly preferred as the germination substratum from the viewpoint of preventing seeds after germination from lodging.

Water is caused to be absorbed by the germination substratum mentioned above by pouring distilled water or phosphate buffer (hereinafter collectively referred to as "germinating liquid") directly onto the germination substratum. The concentration of the phosphate buffer is preferably 0.001-0.03 M. A concentration of 0.04 M is not preferred because the growth after germination may be suppressed at such concentration. The amount of the germinating liquid is preferably about 70-90% of the amount at the level of saturation which can be retained by the germination substratum.

Seeds to be tested are disposed on the germination substratum after the above water absorption. The number of seeds to be disposed can be varied according to the area of the germination substratum and the size of seeds to be tested. The seeds are arranged so that one may not lie on another.

The germination substratum carrying thereon seeds to be tested is placed, after absorption of water, in a hermetic container or, alternatively, it is placed in a hermetic container and then caused to absorb water. The hermetic container is structurally a bag-like or box-like one capable of containing the germination substratum and preferably is a container made of a flexible resin such as polyethylene.

The hermetic container preferably has a structure such that the inside thereof is ordinarily shut off from the open air and, on occasions of necessity, it is possible to discharge the inside air and feed fresh air and/or feed water thereto. More specifically, such a resin-made container as mentioned above is preferably provided with a hermetic zipper capable of being opened and closed. The size of the hermetic container can be arbitrarily selected according to the size of the germination substratum.

The hermetic container with the seed-carrying germination substratum is transferred to a constant-temperature room or the like the temperature in which is controlled at a level suited for the growth of the target pathogen. Outside air is blown into the container using a compressor or the like, the opening/closing zipper is then tightly closed, and the whole is allowed to stand for incubation.

The hermetic container is then allowed to stand in the above-mentioned constant-temperature room or the like for a period necessary for the target pathogen to multiply sufficiently, for example for 10-14 days in the case of bacterial fruit blotch of cucurbit. The hermetic container inside is maintained under environmental conditions such that a high temperature and a high humidity favorable for the multiplication of the pathogen while fresh outside air necessary for the promotion of the growth of seeds after germination and for the prevention of putrefaction is fed from time to time.

The feeding of fresh outside air is carried out in the following manner. The opening/closing zipper of the hermetic container is opened, the hermetic container inside air is discharged into the outside by such an operation as manually pressing the container with care not to destruct the seedlings resulting from germination and, immediately thereafter, the hermetic container is inflated by blowing the outside air thereinto by means of a compressor or the like, followed by tightly closing the opening/closing zipper.

At the time of cotyledon development following germination of the seeds to be tested, an extractant is added to the hermetic container. Like the germinating liquid, distilled water or 0.001-0.03 M phosphate buffer is preferred as the extractant. The extractant, the seeds after germination and the germination substratum are mixed up with stirring and/or pressing in a mixer or the like, and the mixed liquid obtained by this mixing with stirring and/or pressing is used as the material to be tested. The level of addition of the extractant is adjusted according to the size of the germination substratum; preferred is, however, an addition level such that upon slight manual pressing, the extractant oozes out of the germination substratum.

Using the above-mentioned test material, a pathogen detection test is carried out using such a conventional detection method or diagnostic method as (1) identification of colonies grown on medium following plating the test sample liquid onto a semi-selective medium and culture, (2) such a serological method as enzyme-linked immunosorbent assay (ELISA) or (3) a genetic diagnosis using the PCR (polymerase chain reaction) technique, for instance.

When scores of thousands of seeds per lot are to be tested in accordance with the invention, the whole sample seeds are divided into subsample groups each comprising an adequate number of seeds for the practice of the invention and, for each subsample group, a test material is prepared as mentioned above and the test material is tested by the above-mentioned detection method or diagnostic method, and the whole seed sample is evaluated as the set of the subsamples. In the case of a test in which 10,000 seeds per lot being required to be tested, 20 subsample groups each consisting of 500 seeds are prepared and subjected to testing. If the pathogen is detected in only one seed in any of the subsample groups tested, the whole lot of seeds is evaluated as a contaminated seed lot.

EXAMPLES

The following examples illustrate the present invention in further detail. These examples are, however, by no means limitative of the scope of the invention.

Example 1

The pathogen used was *Acidovorax avenae* subsp. *citrulli*, a pathogenic bacterial species causing bacterial fruit blotch, which is generally pathogenic in all plants of the gourd family (Cucurbitaceae). The bacterial fruit blotch-causing bacterial stain was *A. avenae* subsp. *citrulli* (isolate: WM-A) obtained from the Yokohama Plant Protection Station, Ministry of Agricultural, Forestry and Fisheries.

Four paper towels (product of CRECIA, trademark: Kimtowel), each 9.5 cm×13 cm in size, laid one on top of another were used as each germination substratum. A polyethylene bag equipped with a hermetic zipper (product of Seisan Nippon Inc., trademark: Unipack G-8) was used as each hermetic container.

Onto each paper towel assembly was poured 20 ml of distilled water (plot 1) or of one of three phosphate buffer solutions differing in concentration, namely 0.01 M (plot 2), 0.02 M (plot 3) or 0.04 M (plot 4) phosphate buffer (pH 7.4), as the germinating liquid.

For each of the germination substrata for plots 1-4 after watering in the above manner, two of 50 watermelon seeds or two of 50 melon seeds were inoculated with a total inoculum size of 16 cfu (colony forming units) of *A. avenae* subsp. *citrulli*. All the seeds were disposed uniformly all over each germination substratum so as to avoid overlapping of seeds, with the inoculated seeds disposed in the middle of the germination substratum.

Each germination substratum with the seeds disposed thereon was covered with a paper towel of the same kind as used for constituting the germination substratum after wetting with the same liquid as the germinating liquid mentioned above, namely distilled water or one of the phosphate buffer solutions. The paper towel-covered germination substratum was placed in the hermetic container mentioned above. The hermetic container was inflated by blowing the outside air into the same using a compressor and then the zipper was closed tightly and the whole was then allowed to stand in an incubator (product of Nippon Medical & Chemical Instruments, trade name: model EZ NK artificial environmental control system) maintained at a temperature of 28° C. for 10 days.

During the above period of standing, the opening/closing zipper of the hermetic container was opened at 3- or 4-day intervals, the existing air in the container was then discharged by manually pressing the container while avoiding the destruction of seedlings resulting from germination, and fresh outside air was fed using a compressor.

After the above-mentioned period of standing, the hermetic container was opened, 40 ml of 0.01 M phosphate buffer (pH 7.4) was added as the extractant, and the hermetic container was inserted into a mixer (product of IUL, product name: Masticator) and the mixer was operated continuously for 1 minute to thoroughly mix the seeds after germination with the germination substratum.

After mixing up in the above manner, the mixed liquid derived from the germination substratum, seeds, seedlings and extractant was taken out of the hermetic container, and the mixed liquid was diluted with 0.01 M phosphate buffer (pH 7.4) to give a series of dilutions, each at a dilution rate of 10, i.e. from a 10-fold dilution to a 1,000,000-fold dilution. Each dilution was plated onto a semi-selective medium for *A. avenae* subsp. *citrulli* (AacSM), followed by 3 or 4 days of incubation at 40° C. And, the colonies of *A. avenae* subsp. *citrulli* that had appeared were counted, and the number of colonies per milliliter of the mixed liquid (cfu/ml) was calculated and reported as the concentration of *A. avenae* subsp. *citrulli*. The results thus obtained are shown in Table 1. In Table 1, PB represents phosphate buffer.

TABLE 1

| | Aqueous liquid retained by substratum | | | |
|---|---|---|---|---|
| | Distilled water | 0.01 M PB | 0.02 M PB | 0.04 M PB |
| Watermelon | $2 \cdot 10^8$ | $5 \times 10^8$ | $5 \times 10^8$ | $3 \times 10^8$ |
| Melon | $2 \times 10^8$ | $2 \times 10^8$ | $3 \times 10^8$ | $2 \times 10^8$ |

As is evident from Table 1, the growth of *A. avenae* subsp. *citrulli* was observed in each of the germinating liquids used for both watermelon and melon and, in each liquid plot and for each crop, the concentration of *A. avenae* subsp. *citrulli* arrived at a level exceeding $1\times10^8$ cfu per milliliter of the mixed liquid, indicating that seeds infected with *A. avenae* subsp. *citrulli* can be satisfactorily detected by the present method. When 0.04 M phosphate buffer was used, however, there was observed a tendency for the growth of seedlings after germination of melon seeds to be retarded. Thus, the use of distilled water or 0.01 M to 0.02 M phosphate buffer (pH 7.4) was found to be preferred.

Example 2

In Example 2, the same procedure as described in Example 1 was followed except that 0.01 M phosphate buffer (pH 7.4) was used in lieu of the germinating liquid used in Example 1 and the temperature in the hermetic container was set at 20° C. (plot 1), 25° C. (plot 2), 28° C. (plot 3), 30° C. (plot 4) or 35° C. (plot 5) in lieu of 28° C. in Example 1. The results are shown in Table 2.

TABLE 2

| | Standing temperature | | | | |
|---|---|---|---|---|---|
| | 20. | 25. | 28. | 30. | 35. |
| Watermelon | $1 \times 10^6$ | $2 \times 10^8$ | $5 \times 10^8$ | $3 \times 10^8$ | $6 \times 10^7$ |
| Melon | $4 \times 10^7$ | $7 \times 10^7$ | $2 \times 10^8$ | $9 \times 10^8$ | $4 \times 10^8$ |

As is evident from Table 2, the growth of *A. avenae* subsp. *citrulli* was observed in the temperature range of 20-35° C. as set. The temperature range in which the bacterial growth was good was the range of 25-30° C. in the case of watermelon, or the range of 28-35° C. in the case of melon. In each of these temperature plots, the concentration of *A. avenae* subsp. *citrulli* per milliliter of the mixed liquid arrived at a level exceeding $1\times10^8$ cfu, indicating that it is quite possible to detect seeds infected with *A. avenae* subsp. *citrulli*.

Example 3

In Example 3, the procedure of Example 1 was followed in the same manner except that 250 watermelon seeds were used in lieu of the 50 watermelon seeds or 50 melon seeds, that 8 paper towels, each 15 cm×19 cm in size, as laid one on top of another were used in lieu of the four 9.5 cm×13 cm paper towels, that the paper towels were caused to absorb 100 ml, in lieu of 20 ml, of 0.01 M (plot 2) phosphate buffer (pH 7.4), that a polyethylene bag named Unipack J-8 was used in lieu of each Unipack G-8 bag, that the period of standing of the polyethylene bag was 14 days in lieu of 10 days, that 80 ml, in lieu of 40 ml, of 0.01 M phosphate buffer (pH 7.4) was used as the extractant, and that the inoculum size of *A. avenae* subsp. *citrulli* as used was 0.2 cfu (plot 1), 2.0 cfu (plot 2), 20.0 cfu (plot 3) or 0 cfu (no inoculation; plot 4) in lieu of 16 cfu.

In each of plots 1-3, the experiment was repeated 5 times and, in the no-inoculation plot (plot 4), the experiment was repeated 3 times. The ratio "number of repetitions in which *A. avenae* subsp. *citrulli* was detected/number of repetitions of testing" was calculated as the detection rate. The results are shown in Table 3.

TABLE 3

| | Inoculum size (cfu) | Concentration of A. avenae subsp. citrulli (cfu/ml) | Detection rate |
|---|---|---|---|
| Plot 1 | 0.2 | $2.4 \times 10^6$ | 1/5 |
| Plot 2 | 2.0 | $8.7 \times 10^6$ | 5/5 |
| Plot 3 | 20.0 | $1.2 \times 10^7$ | 5/5 |
| Plot 4 | 0.0 | 0.0 | 0/3 |

As shown in Table 3, *A. avenae* subsp. *citrulli* could be detected even when the number of seeds to be tested was increased to 250. In particular, when the inoculum size was 2.0 cfu or larger, *A. avenae* subsp. *citrulli* could be detected stably in all the repeated plots. Further, it is seen that, in each inoculated plot, the bacterial concentration in the mixed liquid finally subjected to testing was at a high multiplication level of $2.4 \times 10^6$ cfu/ml or higher. In the plot inoculated with 2.0 cfu, for instance, the rate of multiplication of *A. avenae* subsp. *citrulli* as calculated on the assumption that the 80 ml of the extractant added in the step of mixing was equal to the total amount of the mixed liquid was $435 \times 10^4$ times.

Example 4

In Example 4, the procedure of Example 3 was followed in the same manner except that 250 melon seeds (plot 1), 250 cucumber seeds (plot 2) or 200 pumpkin seeds (plot 3) were used in lieu of the 250 watermelon seeds, that, in lieu of the inoculation with *A. avenae* subsp. *citrulli,* each plot included a subplot in which one seed contaminated with *A. avenae* subsp. *citrulli* was mixed in and a no treatment subplot with no contaminated seed added, and that the mixed liquid as such was subjected to identification of colonies following plating thereof onto a semi-selective medium (AacSM) or to detection by ELISA or PCR in lieu of the plating of each serial dilution of the mixed liquid onto a semi-selective medium, followed by colony counting. The detection rates attained by means of the semi-selective medium, ELISA technique and PCR technique were calculated in the same manner as in Example 3. The results are shown in Table 4.

The seeds contaminated with *A. avenae* subsp. *citrulli* were prepared as described in Non-Patent Document 1. Thus, intact seeds of each plant species were immersed in a suspension of *A. avenae* subsp. *citrulli* and, after 30 minutes of maintenance in a vacuum desiccator under vacuum, dried under ventilated air to give contaminated seeds. Each of the melon, cucumber and pumpkin seeds used in example 4 was obtained by immersing in a $1 \times 10^5$ cfu/ml bacterial suspension.

The ELISA and PCR methods were carried out as described in the above-cited Non-Patent Document 1. Thus, bacterial cells were recovered from each mixed liquid by centrifugation and suspended in a 1/10 volume of sodium chloride-added 0.02 M phosphate buffer (pH 7.4) for ELISA as supplemented with 0.05% of Tween 20 and, using the suspension as a sample, ELISA was carried out in the manner of DAS-ELISA. In the case of PCR, bacterial cells were recovered from each mixed liquid by centrifugation and, after washing with two portions of 0.01 M phosphate buffer (pH 7.4), suspended in a 1/10 volume of 0.01 M phosphate buffer (pH 7.4) and treated by boiling for 30 minutes and, using the thus-obtained sample as a template, the PCR was carried out.

TABLE 4

| | | A. avenae subsp. citrulli detection rate | | |
|---|---|---|---|---|
| | | Selective medium | ELISA | PCR |
| Plot 1 | With contam. Seed | 5/5 | 5/5 | 5/5 |
| | No treatment | 0/5 | 0/5 | 0/5 |
| Plot 2 | With contam. Seed | 5/5 | 5/5 | 5/5 |
| | No treatment | 0/5 | 0/5 | 0/5 |
| Plot 3 | With contam. Seed | 3/5 | 5/5 | 5/5 |
| | No treatment | 0/5 | 0/5 | 0/5 |

As the results shown in Table 4 indicate, the pathogenic bacteria in question could be detected in all the gourd family crop plants tested, namely melon, cucumber and pumpkin, by the ELISA method and PCR method as well.

Example 5

In Example 5, the procedure of Example 4 was followed in the same manner except that 500 watermelon seeds (plot 1) or 600 melon seeds (plot 2) were used in lieu of the 250 melon seeds, 250 cucumber seeds or 200 pumpkin seeds used in Example 4, that one 27 cm×33 cm paper towel with 30 g of paper towel finely cut by means of a shredder as placed evenly thereon was used as the germination substratum in lieu of the eight 15 cm×19 cm paper towels, that 280 ml, in lieu of 100 ml, of 0.01 M phosphate buffer (pH 7.4) was used as the germinating liquid, that a polyethylene bag named Unipack L-8 was used in lieu of each Unipack J-8 bag, that 200 ml, in lieu of 80 ml, of 0.01 M phosphate buffer (pH 7.4) was used as the extractant, and that the mixed liquid was judged by detection by the PCR method in lieu of the identification of colonies grown on semi-selective medium (AacSM), ELISA or PCR.

The seeds contaminated with *A. avenae* subsp. *citrulli* as used were prepared by the same method as used in Example 4. Each contaminated watermelon seed used in Example 5 was obtained by immersion in a $1 \times 10^7$ cfu/ml bacterial suspension, and each contaminated melon seed in a $1 \times 10^5$ cfu/ml.

As for the PCR method, bacterial cells were recovered from each mixed liquid by centrifugation, washed with two portions of 0.01 M phosphate buffer (pH 7.4), suspended in a 1/10 volume of 0.01 M phosphate buffer (pH 7.4) and treated by 30 minutes of boiling, and the thus-obtained sample liquid was again centrifuged. To the centrifugation supernatant obtained was added insoluble PVP (polyvinylpyrolidone) in an amount of 5 mg per 0.1 ml, and the PVP-supplemented supernatant was used as a template for PCR. The results are shown in Table 5.

TABLE 5

| | | Detection rate by PCR |
|---|---|---|
| Plot 1 | With contaminated seed | 5/5 |
| | No treatment | 0/5 |
| Plot 2 | With contaminated seed | 5/5 |
| | No treatment | 0/5 |

As the results shown in Table 5 indicate, *A. avenae* subsp. *citrulli* could be stably detected by the PCR method even when finely cut paper towel pieces by a shredder were used as the germination substratum or even when the numbers of watermelon seeds and melon seeds were increased to 500 and 600, respectively.

Example 6

Actual seed inspection tests were carried out using seeds currently on the Japanese market. In Example 6, the procedure of Example 1 was followed in the same manner except that 100 seeds each of commercially available melon variety A (plot 1) and melon variety B (plot 2) were used in lieu of the 50 watermelon seeds or 50 melon seeds used in Example 1, that the paper towels assembly was poured 40 ml, in lieu of 20 ml of 0.01 M (plot 2) phosphate buffer (pH 7.4), that each polyethylene bag was allowed to stand for a period of 14 days in lieu of 10 days, and that the inoculation with *A. avenae* subsp. *citrulli* was omitted (no inoculation). The results are shown in Table 6

TABLE 6

| | *A. avenae* subsp. *citrulli* detection rate |
|---|---|
| Plot 1 | 4/10 |
| Plot 2 | 0/10 |

As the results shown in Table 6 indicate, *A. avenae* subsp. *citrulli* was detected in 4 repeated plots among the 10 repeated plots (each plot 1) of the variety A tested. Since the seeds of the variety A melon were of the same lot as the lot of the variety A melon seeds actually used by melon cultivators who had encountered an outbreak of bacterial fruit blotch, it was confirmed that the present method is effective in detecting naturally infected seeds currently distributed in the market.

Example 7

A pathogenic bacterial species (*Acidovorax avenae* subsp. *avenae*) causing bacterial brown stripe disease of rice was used as the pathogen.

In Example 7, the procedure of Example 3 was followed in the same manner except that 300 rice seeds were used in lieu of the 250 watermelon seeds used in Example 3, that one 15 cm×19 cm paper towel with 11.0 g of finely cut paper towel pieces, about 0.4 cm in width and about 4.5 cm in length, uniformly spread thereon was used in lieu of the eight 15 cm×19.5 cm paper towels, that the paper towels were caused to absorb 110 ml, in lieu of 100 ml, of 0.01 M phosphate buffer (pH 7.4), that 60 ml, in lieu of 80 ml, of 0.01 M phosphate buffer (pH 7.4) was used as the extractant, that one rice seed contaminated with *A. avenae* subsp. *avenae* was mixed with each lot of seeds in lieu of the inoculation with *A. avenae* subsp. *citrulli,* and that each mixed liquid as such was tested by PCR in lieu of the plating of each serial dilution of the mixed liquid onto the semi-selective medium, followed by colony counting. In addition to 6 repeated contaminated seed-added plots, the test was repeated without contaminated seed addition in three contaminated seed-free plots, and the *A. avenae* subsp. *avenae* detection ratios were calculated in the same manner as in Example 3.

As for the PCR method, bacterial cells were recovered from each mixed liquid by centrifugation, washed with two portions of 0.01 M phosphate buffer (pH 7.4), resuspended in a $^1/_{10}$ volume of 0.01 M phosphate buffer (pH 7.4) and treated by 15 minutes of boiling. The thus-obtained sample liquid was again centrifuged. To the centrifugation supernatant obtained was added insoluble PVP (polyvinylpyrolidone) in an amount of 5 mg per 0.1 ml, and the PVP-supplemented supernatant was used as a template for PCR. The PCR was carried out as described in W. Y. Song et al. 2004, Detection of *Acidovorax avenae* ssp. *avenae* in rice seeds using bio-PCR. Journal of Phytopathology 152, 667-676.

The seeds contaminated with *A. avenae* subsp. *avenae* were prepared by the method used in Example 4. The contaminated rice seeds used in Example 7 were obtained by immersing in a $1 \times 10^4$ cfu/ml bacterial suspension. The results are shown in Table 7.

TABLE 7

| | *A. avenae* subsp. *avenae* detection rate |
|---|---|
| Contaminated seed added | 6/6 |
| No treatment | 0/3 |

As shown in Table 7, *A. avenae* subsp. *avenae* could be detected even when one rice seed contaminated with *A. avenae* subsp. *avenae* was added to 300 rice seeds. In this example, too, *A. avenae* subsp. *avenae* could multiply at high rates on rice seedlings after germination in hermetic containers allowed to stand, and contaminated seeds could be detected, like in the other cases of combination of gourd seeds with *A. avenae* subsp. *citrulli* in Example 1 and other examples.

What is claimed is:

1. A method of testing seeds possibly bearing a seed-transmissible plant pathogen, comprising;
    a) placing a substratum for germination with seeds disposed uniformly thereon in a hermetic container;
    b) allowing the germination substratum with seeds to stand for a period of time necessary for the seed-transmissible plant pathogen to multiply sufficiently;
    c) periodically discharging air from the hermetic container while avoiding destruction of seedlings resulting from germination of the seeds;
    d) feeding fresh outside air into the hermetic container;
    e) after the period of standing, adding an extractant to the hermetic container;
    f) mixing up the seedlings, the germination substratum, and the extractant with stirring and/or pressing, to thereby obtain a mixed liquid;
    g) removing the mixed liquid from the hermetic container; and
    h) testing for seed-transmissible plant pathogens possibly occurring within said removed mixed liquid.

2. A method of testing seeds as claimed in claim 1, wherein the germination substratum comprises a highly water-absorbing paper and/or a nonwoven fabric and/or cut pieces of a highly water-absorbing paper and/or a nonwoven fabric.

3. A method of testing seeds as claimed in claim 1, wherein during the discharge of air and feeding in of the fresh air, the hermetic container inside air is forcedly replaced with the outside air during the period of seed germination and seedling growth.

4. A method of testing seeds as claimed in claim 1, wherein the seed germination and seedling growth are realized by causing the germination substratum to absorb water or 0.01-0.03 M phosphate buffer.

5. A method of testing seeds as claimed in claim 1, wherein the extractant is water or 0.01-0.03 M phosphate buffer.

6. A method of testing seeds as claimed in claim 1, wherein the pathogen detection using the test material is carried out by identification of colonies grown on medium and/or by a serological method and/or by a genetic diagnosis.

7. A method of testing seeds as claimed in claim 1, wherein the seeds to be tested are seeds of a cucurbitaceous plant.

8. A method of testing seeds as claimed in claim 1, wherein the seeds to be tested are seeds of a poaceous plant.

9. A method of testing seeds as claimed in claim 1, wherein the hermetic container is made of a flexible resin and comprises a hermetic zipper operative to be opened and closed, such that an inside of the hermetic container is ordinarily shut off from outside air by closing the hermetic zipper and is maintained under environmental conditions such that a high temperature and a high humidity are attained for the multiplication of the pathogen.

10. A method of testing seeds as claimed in claim 9, wherein during the period of seed germination and seedling growth, the feeding of fresh outside air further comprises periodically feeding fresh outside air into the hermetic container for the promotion of the growth of seeds after germination and for the prevention of putrefaction.

11. A method of testing as claimed in claim 1, wherein the period of time necessary for the plant pathogen to multiply sufficiently is up to the time of cotyledon development.

* * * * *